United States Patent
Arimoto

(10) Patent No.: US 8,329,022 B2
(45) Date of Patent: Dec. 11, 2012

(54) METHOD FOR QUANTIFYING A CHEMICAL SUBSTANCE BY SUBSTITUTIONAL STRIPPING VOLTAMMETRY AND A SENSOR CHIP USED THEREFOR

(75) Inventor: Satoshi Arimoto, Shiga (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/253,571

(22) Filed: Oct. 5, 2011

(65) Prior Publication Data

US 2012/0216604 A1    Aug. 30, 2012

Related U.S. Application Data

(63) Continuation of application No. PCT/JP2011/003127, filed on Jun. 2, 2011.

(30) Foreign Application Priority Data

Feb. 25, 2011   (JP) ................... 2011-039774

(51) Int. Cl.
*G01N 27/403* (2006.01)

(52) U.S. Cl. ............ 205/775; 204/402; 204/403.01; 204/414

(58) Field of Classification Search ......... 204/412, 204/402, 403.01, 414; 205/775, 789.5, 789
See application file for complete search history.

(56) References Cited

U.S. PATENT DOCUMENTS 5,389,215 A * 2/1995 Horiuchi et al. ............ 205/775

FOREIGN PATENT DOCUMENTS

| EP | 0 569 908 A2 | 11/1993 |
|----|----|----|
| JP | 6-027081 | 2/1994 |
| JP | 2009-156836 | 7/2009 |

OTHER PUBLICATIONS

Senda et al., Stripping Analysis Using ion-transfer voltammetry at liquid/liquid Interface, Collect.Czech.Chem. Commun. 2001, 66, 445-455.*

* cited by examiner

*Primary Examiner* — Alex Noguerola
*Assistant Examiner* — Gurpreet Kaur
(74) *Attorney, Agent, or Firm* — McDermott Will & Emery LLP

(57) ABSTRACT

Provided are a method for quantifying a chemical substance with high accuracy by substitutional stripping voltammetry, and a sensor chip used therefor. A method for quantifying a chemical substance in a sample solution, comprising the following steps: (a) preparing a sensor chip having a stripping gel covered with a protection gel, (b) supplying the sample solution to the surface of the sensor chip to cover the surface with the solution, (c) applying a potential to the first working electrode with potentiostat, and connecting the second working electrode to the stripping electrode to generate reactions on the electrodes, (d) applying a potential to the stripping electrode in a condition where no potential is applied to either the first or the second working electrode to measure a current through the stripping electrode, and (e) calculating, on the basis of the current, the concentration of the oxidation-reduction substance to quantify the chemical substance.

17 Claims, 5 Drawing Sheets

METHOD FOR QUANTIFYING A CHEMICAL SUBSTANCE BY SUBSTITUTIONAL STRIPPING VOLTAMMETRY AND A SENSOR CHIP USED THEREFOR

CROSS REFERENCE TO RELATED APPLICATIONS

This is a continuation of PCT International Application PCT/JP2011/003127 filed on Jun. 2, 2011, claiming priority of Japanese Patent Application No. 2011-039774, filed on Feb. 25, 2011, the disclosures of which applications are hereby incorporated by reference.

TECHNICAL FIELD

This invention relates to a method for quantifying a chemical substance by substitutional stripping voltammetry and a sensor chip used therefor.

BACKGROUND ART

Patent Literature 1 discloses substitutional stripping voltammetry. The substitutional stripping voltammetry allows a chemical substance contained in a solution to be electrochemically quantified with high sensitivity.

FIG. 1 shows the system for the substitutional stripping voltammetry disclosed in the Patent Literature 1.

The system comprises a pair of comb-shaped working electrodes 1, a stripping electrode 2, a reference electrode 3, a counter electrode 4, a solution 5, a stripping liquid 6, a salt bridge 7, and an ion conductor 8, a potentiostat 9, a recorder 10, and a switch box 11.

The solution 5 contains a chemical substance to be quantified and an oxidation-reduction substance. The stripping liquid 6 contains a standard electrolyte and a support electrolyte.

FIG. 2 shows a sensor chip 101a employed for the substitutional stripping voltammetry disclosed in the Patent Literature 1.

The sensor chip 101a comprises a plurality of electrodes 2 to 4 on the surface thereof. Furthermore, the container 64 covers the surface of the sensor chip 101a. The container 64 comprises a first penetrated opening 64a and a second penetrated opening 64b. The solution 5 and the stripping liquid 6 are supplied to the first penetrated opening 64a and the second penetrated opening 64b, respectively.

CITATION LIST

Patent Literature

[Patent Literature 1]
Japanese Patent Publication No. 3289059B.

SUMMARY OF INVENTION

Technical Problem

The desiccation of the stripping liquid 6 changes the concentration of the standard electrolyte. This causes the quantification accuracy of the chemical substance to be lowered.

The purpose of the invention is to provide a method for quantifying a chemical substance with high accuracy by substitutional stripping voltammetry and a sensor chip used therefor.

The present invention is a method for quantifying a chemical substance contained in a sample solution, comprising the following steps (a) to (e):

a step (a) of preparing a sensor chip (300), wherein,
  the sensor chip comprises a substrate (30), a pair of working electrodes (31a/31b), a counter electrode (33), a stripping electrode (34), a stripping gel (35), and a protection gel (36),
  the pair of working electrodes (31a/31b) is composed of a first working electrode (31a) and a second working electrode (31b),
  the surface of the stripping electrode (34) comprises silver,
  the stripping gel (35) covers the stripping electrode (34),
  the stripping gel (35) does not cover the pair of the working electrodes (31a/31b) or the counter electrode (33),
  the stripping gel (35) contains a standard electrolyte and, a hydrophobic or hydrophilic ionic liquid,
  the stripping gel (35) contains no water,
  the hydrophobic or hydrophilic ionic liquid is nonvolatile,
  the hydrophobic or hydrophilic ionic liquid is composed of a cation and an anion,
  the standard electrolyte is composed of the cation and a halide ion,
  the protection gel (36) covers the stripping gel (35),
  the protection gel (36) contains a hydrophobic ionic liquid; however the protection gel (36) contains neither the standard electrolyte nor water,
a step (b) of supplying the sample solution to the surface of the sensor chip to cover the surface with the sample solution, wherein,
  the sample solution contains the chemical substance and an oxidation-reduction substance or contains the chemical substance modified with the oxidation-reduction substance,
a step (c) of applying a potential to the first working electrode (31a) with potentiostat, and connecting the second working electrode (31b) to the stripping electrode (34) to generate reactions represented by the following formulas (I) to (III) in the respective surface of the first working electrode (31a), the second working electrode (31b), and the stripping electrode (34), respectively,
  the first working electrode (31a):

the oxidation-reduction substance (Reductant)→the oxidation-reduction substance (Oxidant)+$e^-$  (I)

the second working electrode (31b):

the oxidation-reduction substance (Oxidant)+$e^-$→the oxidation-reduction substance (Reductant)  (II)

the stripping electrode (34)

the silver+the halide ion→silver halide↓+$e^-$  (III)

wherein, the silver halide is deposited on the surface of the stripping electrode (34),
a step (d) of applying a potential to the stripping electrode (34) in a condition where no potential is applied to either the first working electrode (31a) or the second working electrode (31b) to measure a current flowing through the stripping electrode (34),
a step (e) of calculating the concentration of the oxidation-reduction substance (Reductant) to quantify the chemical substance on the basis of the calculated concentration.

Advantageous Effect of Invention

The present invention provides a method for quantifying a chemical substance with high accuracy using substitutional stripping voltammetry and a sensor chip used therefor.

DESCRIPTION OF EMBODIMENTS

An embodiment of the present invention is described below with reference to FIG. 3.

(Step (a))

First, a sensor chip 300 is prepared.

Figure 1:
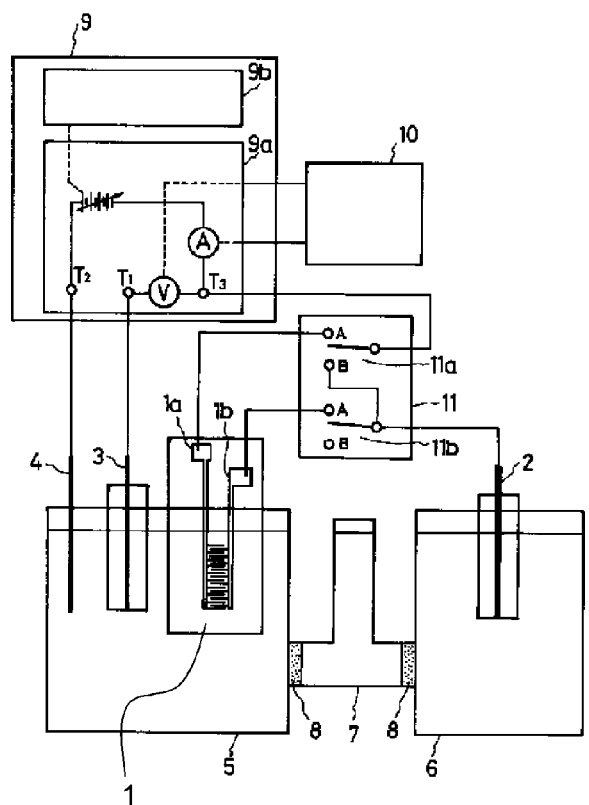
FIG. 1 shows a system for the substitutional stripping voltammetry disclosed in the Patent Literature 1.
Figure 2:
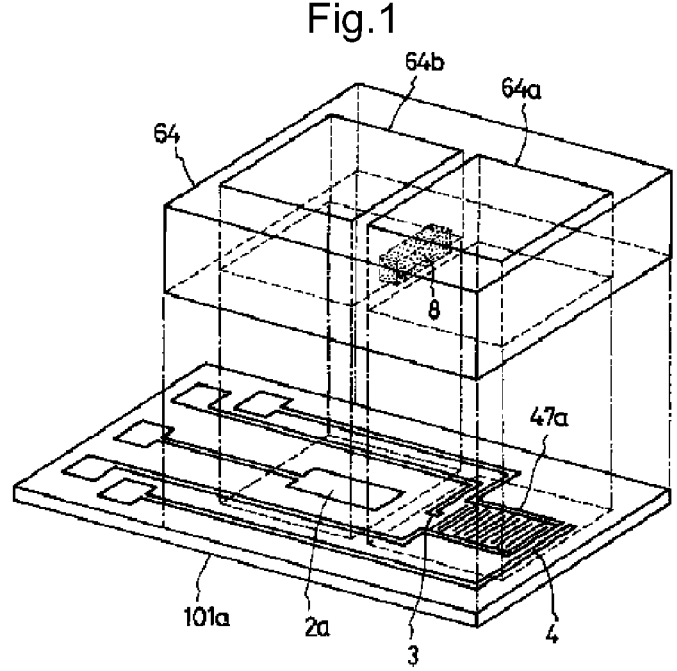
FIG. 2 shows a sensor chip for the substitutional stripping voltammetry disclosed in the Patent Literature 1.
Figure 3:
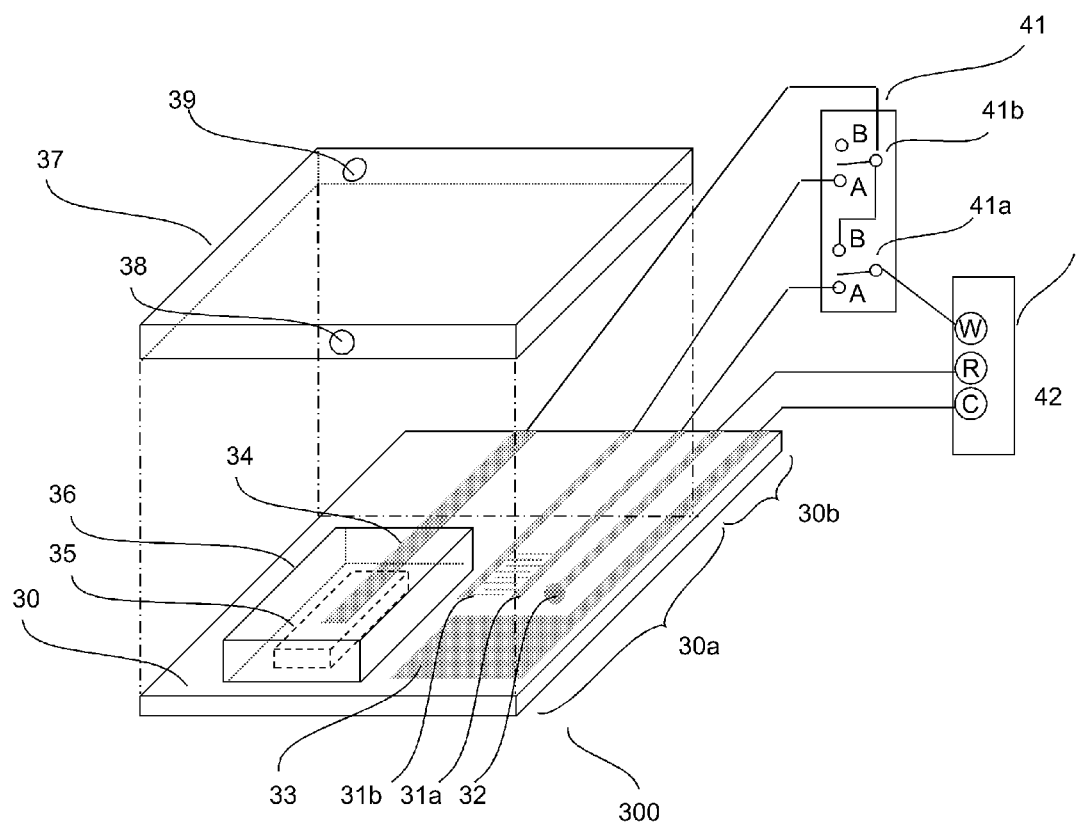
FIG. 3 shows the sensor chip 300 according to the embodiment of the present invention.

FIG. 3 shows the sensor chip 300 according to the embodiment 1. The sensor chip 300 comprises a substrate 30, a pair of comb-shaped working electrodes 31a/31b, a reference electrode 32, a counter electrode 33, a stripping electrode 34, a striping gel 35, a protection gel 36, and a cover 37. The cover 37 comprises an inlet 38 for injecting a sample solution and an air vent 39.

The pair of the comb-shaped working electrodes 31a/31b is composed of a first working electrode 31a and a second working electrode 31b.

The reference electrode 32 is comprised optionally. In light of high accuracy of the quantification, it is preferred that the sensor chip 300 comprises the reference electrode 32.

The substrate 30 comprises an electrode region 30a and a connection region 30b. The cover 37 covers the electrode region 30a on the quantification of the chemical substance, whereas the cover 37 does not cover the connection region 30b.

The pair of comb-shaped electrodes 31a/31b, the reference electrode 32, the counter electrode 33, and the stripping electrode 34 are formed in the electrode region 30a. Each of these electrodes comprises a lead wire(s). All the lead wires do not connect to each other electrically. In the electrode region 30a, they are covered with an insulator film (not shown), which prevents them from coming into contact with the sample solution. All the terminals of the lead wires are extended into the connection region 30b. The connection region 30b is inserted into the connector of the potentiostat 42 shown in FIG. 3.

Examples of the shape of the substrate 30 are a rectangle, a square, and an ellipse. The surface of the substrate 30 comprises an insulator layer (not shown). Preferably, the surface of the substrate 30 is flat in light of formation of the electrodes.

The pair of comb-shaped electrodes 31a/31b are disposed anywhere in the electrode region 30a as long as they do not connect electrically with the stripping gel 35, the protection gel 36, and other electrodes. Preferably, they are disposed in the neighborhood of the center of the electrode region 30a. The examples of the material of the pair of comb-shaped electrodes 31a/31b are gold, platinum, and glassy carbon in light of stability against electrochemical reactions. The pair of comb-shaped electrodes 31a/31b face each other and are engaged.

The reference electrode 32 is also disposed anywhere in the electrode region 30a. Preferably, it is disposed in the neighborhood of the pair of comb-shaped electrodes 31a/31b. On the electrochemical measuring, the reference electrode 32 has the constant potential. An example of the reference electrode 32 is a silver/silver chloride electrode.

The counter electrode 33 may be disposed anywhere in the electrode region 30a. The shape of the counter electrode 33 also is not limited. It is preferred that the area of the counter electrode 33 is approximately twenty to thirty times as large as the area of the pair of comb-shaped electrodes 31a/31b and the area of the stripping electrode 34. Examples of the material of the counter electrode 33 are gold, platinum, and glassy carbon in light of stability against electrochemical reactions similarly to the pair of comb-shaped electrodes 31a/31b.

The stripping electrode 34 comprises silver on the surface thereof.

The stripping gel 35 covers the stripping electrode 34. It is preferred that the stripping gel 35 is located in the neighborhood of the pair of comb-shaped electrodes 31a/31b to lower the resistance therebetween. The stripping gel 35 is preferably a film.

The stripping gel 35 and the protection gel 36 do not cover other electrodes 31 to 33 other than the stripping electrode 34. In case that the stripping gel 35 or the protection gel 36 covers any one of the other electrode 31 to 33, the stripping gel 35 or the protection gel 36 would connect electrically to any one of the other electrodes. This causes the quantification of the chemical substance to be impossible.

The inlet 38 and the air vent 39 may be disposed on the top or side plate of the cover 37. The shapes of the inlet 38 and the air vent 39 are not limited. The cover 37 covers the entire of the electrode region 30a. The cover 37 prevents the sample solution supplied therein from flowing to the connection region 30b and out of the sensor chip 300. The cover 37 is provided optionally. The sample solution may be applied to the surface of the sensor chip 300 without the cover 37.

Next, the stripping gel 35 is described below in more detail.

The stripping gel 35 is obtained by gelling a hydrophobic or hydrophilic ionic liquid containing a standard electrolyte. Namely, the stripping gel 35 contains the standard electrolyte and the hydrophobic or hydrophilic ionic liquid. The hydrophobic or hydrophilic ionic liquid serves as a support electrolyte. A method for gelling a hydrophobic or hydrophilic ionic liquid is not limited. As an example, a polymer is used for gelling. An example of the polymer is Poly(vinylidene fluoride-hexafluoropropylene), Polymethyl methacrylate, Polyacrylonitrile, and Polybutylacrylate.

Next, the protection gel 36 is described below in more detail.

The protection gel 36 is stacked on the stripping gel 35. Namely, the stripping gel 35 is interposed between the protection gel 36 and the stripping electrode 34. As shown in FIG. 3, the protection gel 36 covers the entire of the stripping gel 35 in such a manner that the stripping gel 35 is hidden completely by the protection gel 36.

The protection gel 36 is obtained by gelling a hydrophobic ionic liquid similarly to the stripping gel 35. The protection gel 36 does not contain the standard electrolyte. The hydrophobic ionic liquid serves as a support electrolyte similarly to the stripping gel 35. The protection gel 36 does not contain the hydrophilic ionic liquid.

The hydrophobic ionic liquid is composed of the following cation and the following anion.

Cation:
(1) 1—$R_1$-2-$R_2$-3-$R_3$-imidazolium ion ($R_1$ represents lower alkyl group (carbon number is 1-6), $R_2$ represents hydrogen or methyl group, $R_3$ represents an alkyl group and may contain a hetero atom),
(2) N—$R_4$-isoquinolium ion ($R_4$ represents an alkyl group and may contain a hetero atom),
(3) N—$R_5$-pridinium ion ($R_5$ represents an alkyl group and may contain a hetero atom),
(4) N,N—$R_6$,$R_7$-pyrrolidinium ion ($R_6$ represents lower alkyl group (carbon number is 1-6), $R_7$ represents an alkyl group and may contain a hetero atom),
(5) N,N—$R_8$,$R_9$-piperidinium ion ($R_8$ represents lower alkyl group (carbon number is 1-6), $R_9$ is an alkyl group and may contain a hetero atom), or
(6) $R_{10}$,$R_{11}$,$R_{12}$,$R_{13}$-ammonium ion ($R_{10}$, $R_{11}$, $R_{12}$, and $R_{13}$ represents an alkyl group, a phenyl group, or a benzyl group independently, which may contain a hetero atom),
Anion:
(1) Bis(trifluoromethanesulfonyl)imide ion
(2) Triflate ion, or
(3) Bis(pentafluoroethanesulfonyl)imide ion More specifically, the ionic liquid is exemplified below.
1,3-Dimethylimidazolium bis(trifluoromethanesulfonyl)imide,
1-Ethyl-3-methylimidazolium bis(trifluoromethanesulfonyl)imide,
1-Ethyl-3-methylimidazolium triflate,
1-Ethyl-3-methylimidazolium bis(pentafluoroethanesulfonyl)imide,
1,3-Diethylimidazolium bis(trifluoromethanesulfonyl)imide,
1,3-Diethylimidazolium triflate,
1-Butyl-3-ethylimidazolium triflate,
1,2-Dimethyl-3-ethylimidazolium bis(trifluoromethanesulfonyl)imide,
1-Butyl-3-methylimidazolium bis(trifluoromethanesulfonyl)imide,
1-Butyl-3-methylimidazolium triflate,
1-isoPropyl-3-methylimidazolium bis(trifluoromethanesulfonyl)imide,
1,2-Dimethyl-3-propylimidazolium bis(trifluoromethanesulfonyl)imide,
N,N-Propylmethylpyrrolidinium bis(trifluoromethanesulfonyl)imide,
Propyltrimethyammonium bis(trifluoromethanesulfonyl)imide,
N,N-Methylpropylpiperidinium bis(trifluoromethanesulfonyl)imide, and
N-Butylpyridinium bis(trifluoromethanesulfonyl)imide The hydrophilic ionic liquid is composed of the following cation and the following anion.
Cation:
(1) 1—$R_1$-2-$R_2$-3-$R_3$-imidazolium ion ($R_1$ represents lower alkyl group (carbon number is 1-6), $R_2$ represents hydrogen or methyl group, $R_3$ represents an alkyl group and may contain a hetero atom),
(2) N—$R_4$-isoquinolium ion ($R_4$ represents an alkyl group and may contain a hetero atom),
(3) N—$R_5$-pridinium ion ($R_5$ represents an alkyl group and may contain a hetero atom),
(4) N,N—$R_6$,$R_7$-pyrrolidinium ion ($R_6$ represents lower alkyl group (carbon number is 1-6), $R_7$ represents an alkyl group and may contain a hetero atom),
(5) N,N—$R_8$,$R_9$-piperidinium ion ($R_8$ represents lower alkyl group (carbon number is 1-6), $R_9$ is an alkyl group and may contain a hetero atom), or
(6) $R_{10}$,$R_{11}$,$R_{12}$,$R_{13}$-ammonium ion ($R_{10}$, $R_{11}$, $R_{12}$, and $R_{13}$ represents an alkyl group, a phenyl group, or a benzyl group independently, which may contain a hetero atom),
Anion:
(4) Tetrafluoroborate ion
(5) Halide ion More specifically, the ionic liquid is exemplified below.
1-Ethyl-3-methylimidazolium tetrafluoroborate
1-Butyl-3-methylimidazolium tetrafluoroborate
1-Methyl-3-propylimidazolium tetrafluoroborate
1-Butyl-3-methylimidazolium iodide
1-Hexyl-3-methylimidazolium bromide
1-Hexyl-3-methylimidazolium chloride
1-Octyl-3-methylimidazolium chloride
N-Hexylpyridinium chloride The standard electrolyte is composed of the above-mentioned cation and a halide ion. The halide ion denotes chloride, bromide, or iodide ion.

It is preferred that the standard electrolyte has an identical or similar cation to that of the hydrophobic or the hydrophilic ionic liquid comprised in the stripping gel in light of solubility. For example, in a case where the ionic liquid is 1-Butyl-3-methylimidazolium bis(trifluoromethanesulfonyl)imide, it is preferable that the standard electrolyte is 1-Butyl-3-methylimidazolium halide (Preparation Method of the Sensor Chip)

A procedure to prepare the sensor chip of the present embodiment is described below.

(Formation of Electrodes)

An insulated substrate coated with a photoresist is exposed to an ultraviolet through a mask for patterning, followed by alkaline developing. A metal is sputtered on the patterned substrate. The residue photoresist is melted in an organic solvent to remove the unnecessary metal. The entire surface of the substrate is coated with an insulating film. The insulating film over the electrodes is removed by dry etching to form the pair of comb-shaped electrodes 31*a*/31*b*, the reference electrode 32, the counter electrode 33 and the stripping electrode 34. The Ag/AgCl electrode is formed by applying an Ag/AgCl paste on the reference electrode 32.

(Formation of Stripping Gel 35)

The stripping gel 35 may be formed as below.

First, Poly(vinylidene fluoride-hexafluoropropylene) is dissolved in acetone with an ultrasonic wave while ice cooling to prepare an acetone solution. 1-Butyl-3-methylimidazolium bis(trifluoromethanesulfonyl)imide containing 1-Butyl-3-methylimidazolium iodide is added to the acetone solution. Subsequently, the acetone solution is stirred and dropped on the stripping electrode 34. Finally, the acetone is evaporated to form the stripping gel 35.

(Formation of Protection Gel 36)

The protection gel 36 may be formed as below.

Poly(vinylidene fluoride-hexafluoropropylene) is dissolved in acetone with an ultrasonic wave while ice cooling to prepare an acetone solution similarly to the case of the stripping gel 35. 1-Butyl-3-methylimidazolium bis(trifluoromethanesulfonyl)imide is added to the acetone solution. Subsequently, the acetone solution is stirred and dropped on the stripping gel 35. Finally, the acetone is evaporated to form the protection gel 36.

(Step (b))

A sample solution is supplied to the surface of the above-mentioned sensor chip 300 to cover the surface with the sample solution.

The sample solution contains a chemical substance to be quantified according to the present invention. Examples of the chemical substance are an antigen, an antibody, a nucleic acid, a cell, bacteria, virus, a hapten, and sugar.

Preferably, the cover 37 is provided with the sensor chip 300. The sample solution supplied through the inlet 38 covers the surface of the sensor chip 300. The air in the space between the cover 37 and the sensor chip 300 is discharged through the air vent 39. More preferably, the space between the cover 37 and the sensor chip 300 is filled up with the sample solution. This allows the volume of the liquid solution to be constant.

The sample solution contains a chemical substance to be quantified and an oxidation-reduction substance. In the present invention, the sample solution contains the oxidation-reduction substance in the reduction condition. The chemical substance to be quantified and an oxidation-reduction substance may be distinct. For example, the chemical substance to be quantified is an enzyme, and the oxidation-reduction substance is an electric mediator such as potassium ferrocyanide. Or, the chemical substance to be quantified may be modified with the oxidation-reduction substance. For example, the protein modified with a ferrocenecarboxylic acid (hereinafter, "FcCOOH") is exemplified.

The substitutional stripping voltammetry comprises a step (c) and a step (d).

(Step (c))

In the step (c), the switch 41a and the switch 41b are connected to the respective terminals A, and a constant potential is applied to the first working electrode 31a. Furthermore, the second working electrode 31b is electrically connected to the stripping electrode 34 to form a redox cycle between the pair of comb-shaped electrodes 31a/31b.

In a case that the oxidation-reduction substance is ferrocenecarboxylic acid, the following reactions represented by the following chemical formulas (I) to (III) are caused on the comb-shaped electrodes 31a, the comb-shaped electrodes 31b, and the stripping electrode 34.

Comb-shaped working electrode 31a:

$$Fc^{2+}COOH \text{ (Reductant)} \rightarrow Fc^{3+}COOH \text{ (Oxidant)} + e^- \quad (I)$$

Comb-shaped working electrode 31b:

$$Fc^{3+}COOH \text{ (Oxidant)} + e^- \rightarrow Fc^{2+}COOH \text{ (Reductant)} \quad (II)$$

Stripping electrode 34:

$$Ag + X^- \rightarrow AgX\downarrow + e^- \quad (III)$$

X is I, Br, or Cl.

Silver halide is deposited on the surface of the stripping electrode 34, which is composed of silver.

(Step (d))

In the step (d), the switch 41a and the switch 41b are connected to the respective terminals B. No potential is applied to either the first working electrode 31a or the second working electrode 31b. The stripping electrode 34 is swept with the potentiostat 42 to cause the silver halide, which has been deposited, to be dissolved in the sample solution as shown in the following chemical formula (IV).

Stripping electrode 34:

$$AgX + e^- \rightarrow Ag + X^- \quad (IV)$$

The stripping gel 35 contains no water. The hydrophobic and hydrophilic ionic liquids are nonvolatile. Accordingly, unlike prior arts, the desiccation of the stripping gel 35 is prevented in the step (c) and in the step (d).

The stripping gel 35 does not contact directly with the sample solution. Accordingly, the elution of the standard electrolyte from the stripping gel 35 is prevented. This allows the concentration of the standard electrolyte to be maintained.

As a result, the quantification of the chemical substance is allowed to be more accurate. This characterizes the present invention.

In step (c) where a longer period of constant potential is applied, the higher sensitivity is achieved, since the deposition amount of silver halide is increased.

(Step (e))

The amount of the current flowing on the dissolution in the step (d) is proportional to the deposited amount of the silver halide. The deposited amount of the silver halide is proportional to the product of the concentration of the oxidation-reduction substance (Reductant) by the period when the potential is applied in the step (c). Namely, the following equation is satisfied.

(the deposition amount of the silver halide)=(the concentration of the oxidation-reduction substance (Reductant))·(the period when the potential is applied in the step (c))

Accordingly, the concentration of the oxidation-reduction substance (Reductant) is calculated from the amount of the current flowing in the step (d). The chemical substance is quantified on the basis of the concentration of the oxidation-reduction substance (Reductant). Needless to say, similarly to the case of a typical procedure, when the chemical substance is quantified from the current, a standard curve which has been prepared is used.

Reference Example

A reference example of the present invention is described below.

First, a first working electrode 50 was prepared.

Figure 4:
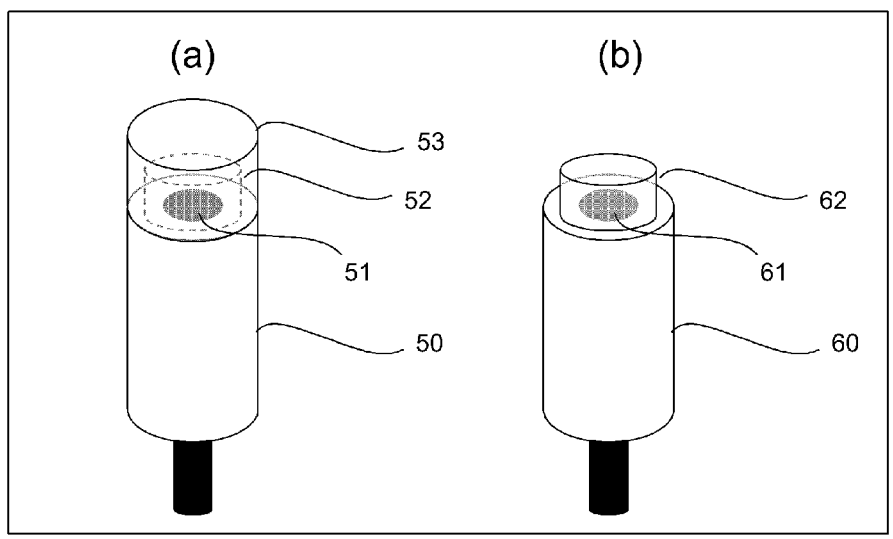
FIG. 4 shows the first working electrode 50 and the second working electrode 60 in the reference example and in the comparative example

FIG. 4(a) shows the first working electrode 50 according to the present reference example The first working electrode 50 comprised a silver plate 51, a stripping gel 52, and a protection gel 53.

(Preparation of the First Working Electrode 50)

The first working electrode 50 was prepared as below.

Fifty milligrams of Poly(vinylidene fluoride-hexafluoropropylene) (available from Aldrich) was dissolved in acetone by ultrasonic irradiation on ice cooling in a closed container to prepare an acetone solution. The copolymer had an average molecular weight of 470,000. Fifty microliters of 1-Butyl-3-methylimidazolium bis(trifluoromethanesulfonyl)imide (available from TOKYO CHEMICAL INDUSTRY CO., LTD.) containing 100 mM of 1-Butyl-3-methylimidazolium iodide (available from Wako Pure Chemical Industries, Ltd.) was added to the acetone solution and stirred well. Thus, a first stock solution was prepared.

Similarly to the case of first stock solution, fifty microliters of 1-Butyl-3-methylimidazolium bis(trifluoromethanesulfonyl)imide was also added to the acetone solution and stirred well. Thus, a second stock solution was prepared.

Ten microliters of the first stock solution was dropped on the silver plate 51, which had a diameter of 3.0 millimeters. The acetone was evaporated to form the stripping gel 52 on the silver plate 51. Next, forty microliters of the second stock solution was dropped in such a manner that the second solution covered the stripping gel 52. The acetone was evaporated to form the protection gel 53. Thus, the first working electrode 50 was obtained.

(Electrochemical Measurement)

Electrochemical measurement was conducted as below.

Figure 5:
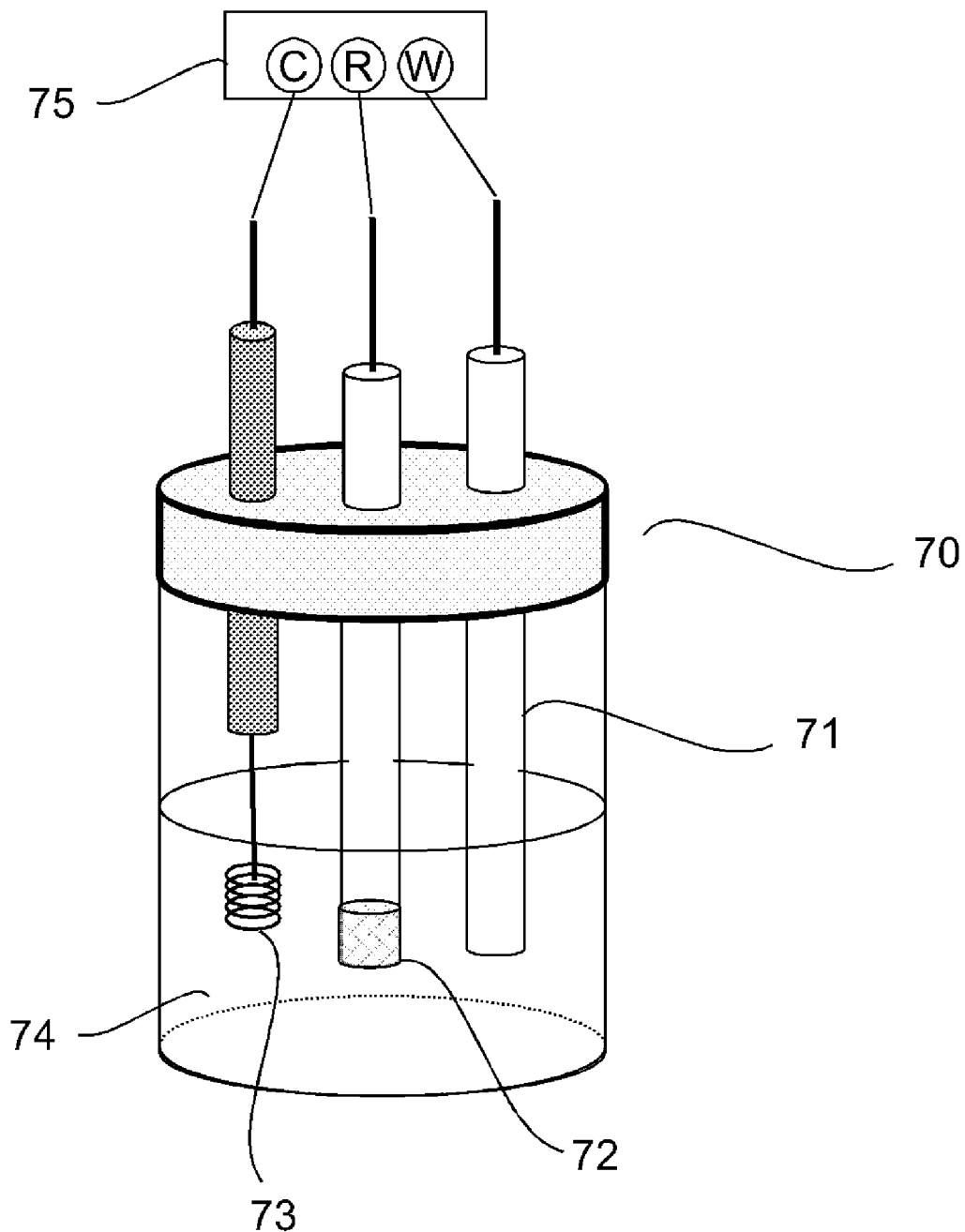
FIG. 5 shows the electrochemical measurement cell 70 according to the reference example and the comparative example

FIG. 5 shows an electrochemical cell 70 according to the present reference example. The electrochemical cell 70 comprised a working electrode 71, a reference electrode 72, a counter electrode 73, an electrolyte solution 74, and potentiostat 75.

The working electrode 71 was the first working electrode 50. The reference electrode 72 was a silver/silver chloride electrode. The counter electrode 73 was a platinum wire. The electrolyte solution 74 was Dulbecco's Phosphate Buffered Saline (D-PBS: 7 mM NaCl, 2.7 mM KCl, 10 mM $Na_2HPO_4$, 1.8 mM $KH_2PO_4$).

The potential of the first working electrode 50 was swept with the potentiostat 75 (available from BAS, trade name: ALS-660A) at a scan rate of 10 mV/s for twenty cycles.

FIG. 6(a) shows the first, third, fifth and seventh cycles of the cyclic voltammograms obtained with the first working electrode 50. Redox current peaks around −0.38 V (vs. Ag/AgCl) were observed. These currents are derived from the oxidization-reduction reaction represented by the following chemical formula (V).

$$Ag-I^- \leftrightarrows AgI + e^- \quad\quad (V)$$

Figure 7:
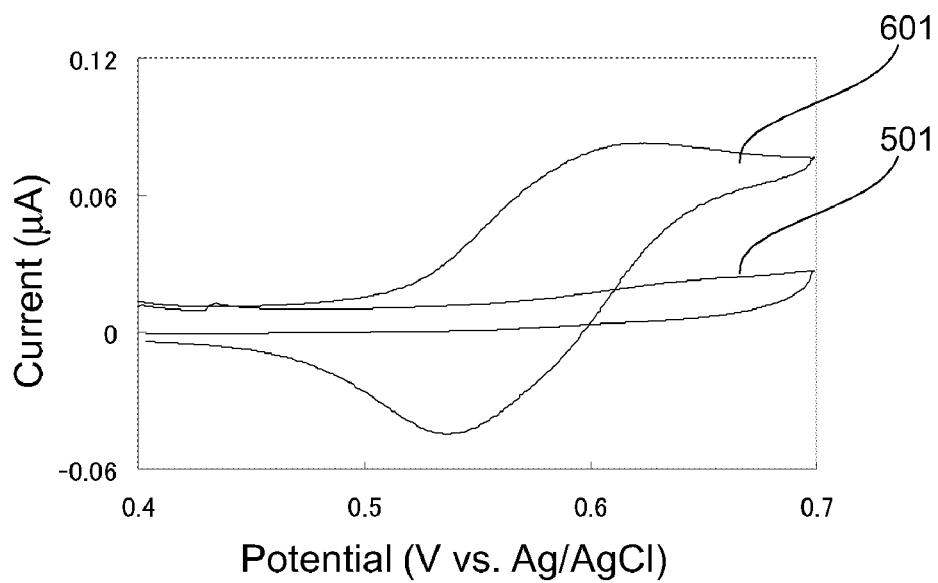
FIG. 7 shows the cyclic voltammograms measured in the saline.

The current 501 in FIG. 7 shows a cyclic voltammogram at a scan rate of 10 mV/s with use of the electrochemical cell 70 shown in FIG. 5. In this cyclic voltammogram, a gold plate with a diameter of 1.6 mm was used as a working electrode 71. The electrolyte solution was a saline which had been used for the cyclic voltammetry with the first working electrode 50. The current 501 shown in FIG. 7 means that the oxidation-reduction (Namely, redox) reaction did not occur.

Comparative Example

A comparative example of the present invention is described below.

(Preparation a Second Working Electrode 60)

The second working electrode 60 was prepared similarly to the case of the first working electrode 50 except that no protection gel was formed.

FIG. 4(b) shows the second working electrode 60 according to the comparative example. The second working electrode 60 comprised a silver plate 61, and a stripping gel 62. Unlike the first working electrode 50, the second working electrode 60 comprised no protection gel.

(Electrochemical Measurement)

Electrochemical measurement was conducted with the electrochemical cell 70 shown in FIG. 5 similarly to the case of the first working electrode 50. The second working electrode 60 was used as the working electrode 71.

FIG. 6(b) shows the first cycle 81, the third cycle 82, the fifth cycle 83, and the seventh cycle 84 of the cyclic voltammograms obtained with the second working electrode 60. Redox current peaks around −0.38 V (vs. Ag/AgCl) derived from the reaction formula (V) were observed similarly to the case of the first working electrode 50. The redox current was gradually decreased.

The current 601 in FIG. 7 shows a cyclic voltammogram at the scan rate of 10 mV/s obtained in the saline which had been used for the cyclic voltammetry with the second working electrode 60. Unlike the current 501, the current 601 means that the oxidation-reduction (Namely, redox) reaction occurred.

Figure 6:
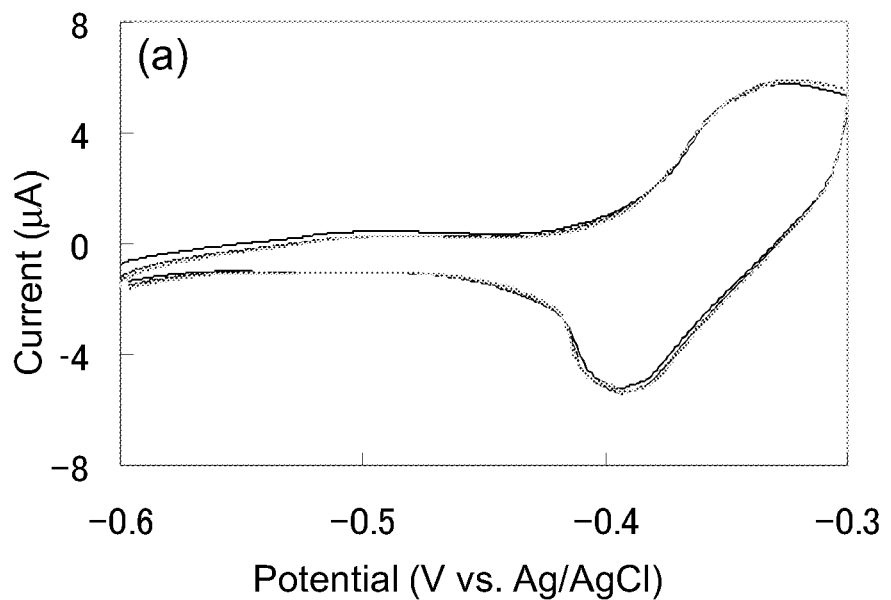
FIG. 6 shows cyclic voltammograms with use of the first working electrode 50 and the second working electrode 60.
Figure 6:
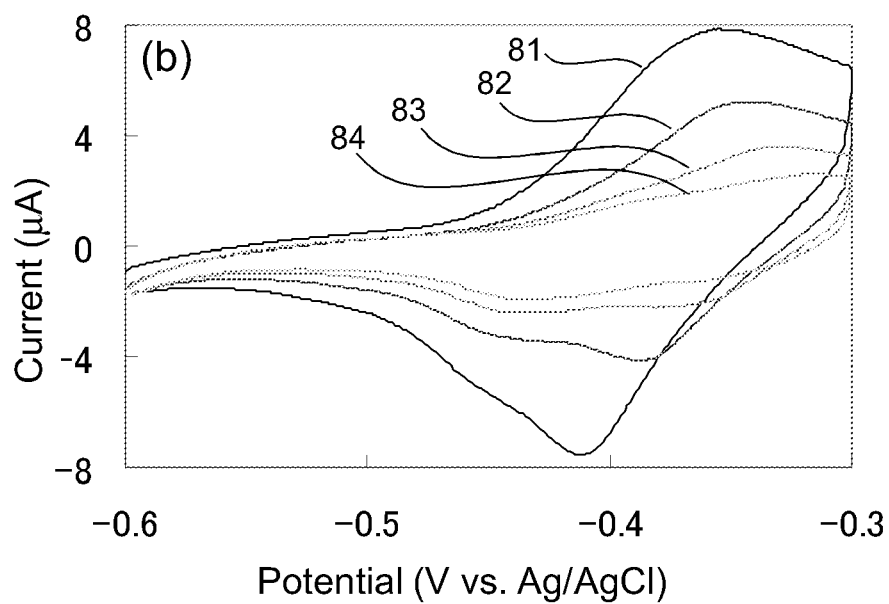
Figure 8:
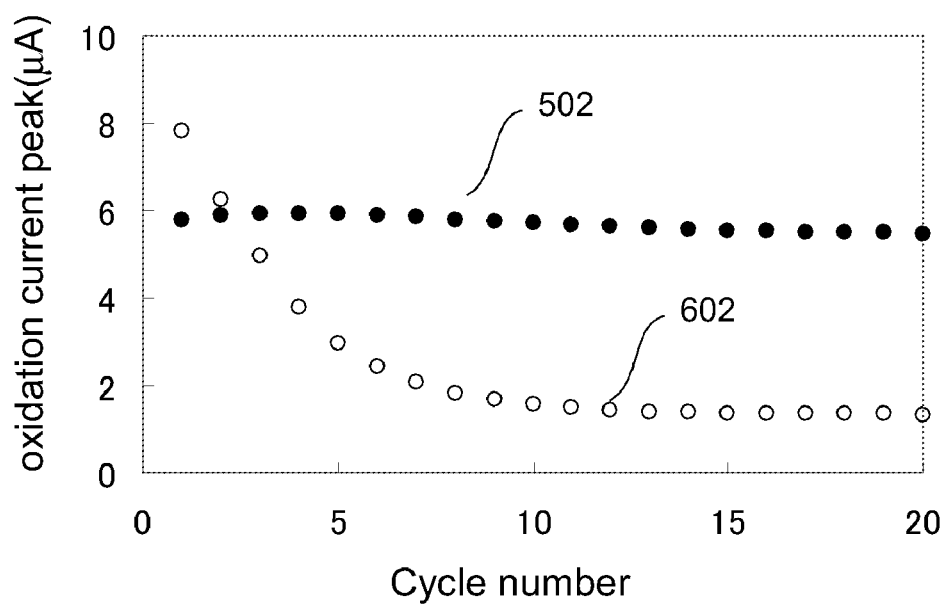
FIG. 8 shows the plots of the peak values of the anodic current of the cyclic voltammograms in FIG. 6 versus cycle numbers.

FIG. 8 shows the plots of the peak values of the anodic current of the cyclic voltammograms in FIG. 6 versus cycle numbers. The plots 502 and the plots 602 show the results with the first working electrode 50 and the second working electrode 60, respectively.

Plots 502 showed a substantially constant anodic current peak value. This result reveals that the concentration of iodide ion contained in the stripping gel 52 was maintained to be constant.

Plots 602 showed that an anodic current peak value is gradually decreased when the measurement cycles were increased. This result reveals that the iodide ion contained in the stripping gel 62 was eluted into the electrolyte solution 74.

The stripping gel 52 did not contact directly with the sample solution because of the protection gel 53. Accordingly, the elution of the iodide ion from the stripping gel 52 was prevented. This allowed the concentration of iodide ion contained in the stripping gel 52 to be maintained constantly. This characterized the present invention.

INDUSTRIAL APPLICABILITY

The present invention provides a method for quantifying a chemical substance in high accuracy by substitutional stripping voltammetry and a sensor chip used therefor.

REFERENCE SIGNS LIST

1: Comb-shaped working electrodes
2: Stripping electrode
3: Reference electrode
4: Counter electrode
5: Solution
6: Stripping liquid
7: Salt bridge
8: Ion conductor
9: Potentiostat
10: Recorder
11: Switch box
101a: Sensor chip
2a: Stripping electrode
47a: Comb-shaped working electrodes
64: Container
300: Sensor chip
30: Substrate
30a: Electrode region
30b: Connection region
31a: Comb-shaped working electrodes
31b: Comb-shaped working electrodes
32: Reference electrode
33: Counter electrode
34: Stripping electrode
35: Stripping gel
36: Protection gel
37: Cover
38: Inlet
39: Air vent
41: Switch box
42: Potentiostat
50: Working electrode
51: Silver plate
52: Stripping gel
53: Protection gel
60: Working electrode
61: Silver
62: Stripping gel
70: Electrochemical cell
71: Working electrode
72: Reference electrode
73: Counter electrode
74: Electrolyte solution
75: Potentiostat 81: Cyclic voltammogram
82: Cyclic voltammogram
83: Cyclic voltammogram
84: Cyclic voltammogram
501: Cyclic voltammogram
601: Cyclic voltammogram
502: Plots
602: Plots

The invention claimed is:

1. A method for quantifying a chemical substance contained in a sample solution, comprising the following steps (a) to (e):

a step (a) of preparing a sensor chip, wherein,
the sensor chip comprises a substrate, a pair of working electrodes, a counter electrode, a stripping electrode, a stripping gel, and a protection gel,
the pair of working electrodes is composed of a first working electrode and a second working electrode,
the surface of the stripping electrode comprises silver,
the stripping gel covers the stripping electrode,
the stripping gel does not cover the pair of working electrodes or the counter electrode,
the stripping gel contains a standard electrolyte and, a hydrophobic or hydrophilic ionic liquid,
the stripping gel contains no water,
the hydrophobic or hydrophilic ionic liquid is nonvolatile,
the hydrophobic or hydrophilic ionic liquid is composed of a cation and an anion,
the standard electrolyte is composed of the cation and a halide ion,
the protection gel covers the stripping gel,
the protection gel contains a hydrophobic ionic liquid; however the protection gel contains neither the standard electrolyte nor water,
a step (b) of supplying the sample solution to the surface of the sensor chip to cover the surface with the sample solution, wherein,
the sample solution contains the chemical substance and an oxidation-reduction substance or contains the chemical substance modified with the oxidation-reduction substance,
a step (c) of applying a potential to the first working electrode with potentiostat, and connecting the second working electrode to the stripping electrode to generate reactions represented by the following formulas (I) to (III) in the respective surface of the first working electrode, the second working electrode, and the stripping electrode, respectively,
the first working electrode:

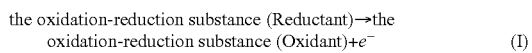

$$\text{the oxidation-reduction substance (Reductant)} \rightarrow \text{the oxidation-reduction substance (Oxidant)} + e^- \quad (I)$$

the second working electrode:

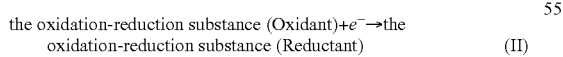

$$\text{the oxidation-reduction substance (Oxidant)} + e^- \rightarrow \text{the oxidation-reduction substance (Reductant)} \quad (II)$$

the stripping electrode

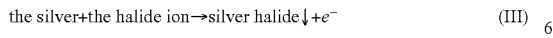

$$\text{the silver} + \text{the halide ion} \rightarrow \text{silver halide} \downarrow + e^- \quad (III)$$

wherein, the silver halide is deposited on the surface of the stripping electrode,
a step (d) of applying a potential to the stripping electrode in a condition where no potential is applied to either the first working electrode or the second working electrode to measure a current flowing through the stripping electrode, a step (e) of calculating the concentration of the oxidation-reduction substance (Reductant) to quantify the chemical substance on the basis of the calculated concentration.

2. The method according to claim 1, wherein,
the sensor chip further comprises a cover with an inlet,
a space is formed between the cover and the sensor chip,
in the step (b), the sample solution is supplied through the inlet to the surface of the sensor chip.

3. The method according to claim 2, wherein,
the cover further comprises an air vent,
in the step (b), the air which has filled the space is discharged through the air vent.

4. The method according to claim 2, wherein,
after the step (b), the space is filled with the sample solution.

5. The method according to claim 1, wherein,
the cation and the anion comprised in the hydrophobic ionic liquid are selected from the following groups (I) and (II), respectively:

Group (I):
(1) 1-$R_1$-2-$R_2$-3-$R_3$-imidazolium ion ($R_1$ represents methyl group or butyl group, $R_2$ represents hydrogen or methyl group, $R_3$ represents an alkyl group and may contain a hetero atom),
(2) N—$R_4$-isoquinolium ion ($R_4$ represents an alkyl group and may contain a hetero atom),
(3) N—$R_5$-pridinium ion ($R_5$ represents an alkyl group and may contain a hetero atom),
(4) N,N—$R_6$,$R_7$-pyrrolidinium ion ($R_6$ represents methyl group, ethyl group, propyl group, isopropyl group, or butyl group, $R_7$ represents an alkyl group and may contain a hetero atom),
(5) N,N—$R_8$,$R_9$-piperidinium ion ($R_8$ represents methyl group or butyl group, $R_9$ is an alkyl group and may contain a hetero atom), or
(6) $R_{10}$,$R_{11}$,$R_{12}$,$R_{13}$-ammonium ion ($R_{10}$, $R_{11}$, $R_{12}$, and $R_{13}$ represents an alkyl group, a phenyl group, or a benzyl group independently, which may contain a hetero atom), Group (II):
(1) Bis(trifluoromethanesulfonyl)imide ion,
(2) Triflate ion, or
(3) Bis(pentafluoroethanesulfonyl)imide ion.

6. The method according to claim 1, wherein,
the hydrophobic ionic liquid is selected from the followings:
1,3-Dimethylimidazolium bis(trifluoromethanesulfonyl)imide,
1-Ethyl-3-methylimidazolium bis(trifluoromethanesulfonyl)imide,
1-Ethyl-3-methylimidazolium triflate,
1-Ethyl-3-methylimidazolium bis(pentafluoroethanesulfonyl)imide,
1,3-Diethylimidazolium bis(trifluoromethanesulfonyl)imide,
1,3-Diethylimidazolium triflate,
1-Butyl-3-ethylimidazolium triflate,
1,2-Dimethyl-3-ethylimidazolium bis(trifluoromethanesulfonyl)imide,
1-Butyl-3-methylimidazolium bis(trifluoromethanesulfonyl)imide,
1-Butyl-3-methylimidazolium triflate,
1-isoPropyl-3-methylimidazolium bis(trifluoromethanesulfonyl)imide,
1,2-Dimethyl-3-propylimidazolium bis(trifluoromethanesulfonyl)imide, N,N-Propylmethylpyrrolidinium bis(trifluoromethane-sulfonyl)imide,
Propyltrimethyammonium bis(trifluoromethanesulfonyl)imide,
N,N-Methylpropylpiperidinium bis(trifluoromethane-sulfonyl)imide, or
N-Butylpyridinium bis(trifluoromethanesulfonyl)imide.

7. The method according to claim 1, wherein,
the cation and the anion comprised in the hydrophilic ionic liquid are selected from the following groups (I) and (III), respectively:
Group (I):
(1) 1-$R_1$-2-$R_2$-3-$R_3$-imidazolium ion ($R_1$ represents methyl group or butyl group, $R_2$ represents hydrogen or methyl group, $R_3$ represents an alkyl group and may contain a hetero atom),
(2) N—$R_4$-isoquinolium ion ($R_4$ represents an alkyl group and may contain a hetero atom),
(3) N—$R_5$-pridinium ion ($R_5$ represents an alkyl group and may contain a hetero atom),
(4) N,N—$R_6$,$R_7$-pyrrolidinium ion ($R_6$ represents methyl group, ethyl group, propyl group, isopropyl group, or butyl group, $R_7$ represents an alkyl group and may contain a hetero atom),
(5) N,N—$R_8$,$R_9$-piperidinium ion ($R_8$ represents methyl group or butyl group, $R_9$ is an alkyl group and may contain a hetero atom), or
(6) $R_{10}$,$R_{11}$,$R_{12}$,$R_{13}$-ammonium ion ($R_{10}$, $R_{11}$, $R_{12}$, and $R_{13}$ represents an alkyl group, a phenyl group, or a benzyl group independently, which may contain a hetero atom),
Group (III):
(4) Tetrafluoroborate ion, or
(5) Halide ion.

8. The method according to claim 1, wherein,
the hydrophilic ionic liquid is selected from the following:
1-Ethyl-3-methylimidazolium tetrafluoroborate,
1-Butyl-3-methylimidazolium tetrafluoroborate,
1-Methyl-3-propylimidazolium tetrafluoroborate,
1-Butyl-3-methylimidazolium iodide,
1-Hexyl-3-methylimidazolium bromide,
1-Hexyl-3-methylimidazolium chloride,
1-Octyl-3-methylimidazolium chloride, or
N-Hexylpyridinium chloride.

9. The method according to claim 1, wherein,
the protection gel covers the entire of the stripping gel in such a manner that the stripping gel is hidden by the protection gel completely.

10. A sensor chip for a substitutional stripping voltammetry, comprising:
a substrate,
a pair of working electrodes,
a counter electrode,
a stripping electrode, and
and a stripping gel, wherein
the pair of working electrode is composed of a first working electrode and a second working electrode,
the surface of the stripping electrode comprises silver,
the stripping gel covers the stripping electrode,
the stripping gel does not cover the pair of the working electrodes or the counter electrode,
the stripping gel contains a standard electrolyte and, a hydrophobic or hydrophilic ionic liquid,
the hydrophobic or hydrophilic ionic liquid comprises a cation and an anion,
the standard electrolyte contains the cation and a halide ion,
the protection gel covers the stripping gel,
the protection gel contains a hydrophobic ionic liquid; however the protection gel contains neither the standard electrolyte nor water.

11. The sensor chip according to claim 10, wherein,
the sensor chip (300) further comprises a cover with an inlet,
a space is formed between the cover and the sensor chip.

12. The sensor chip according to claim 11, wherein,
the cover further comprises an air vent.

13. The sensor chip according to claim 10, wherein,
the cation and the anion comprised in the hydrophobic ionic liquid are selected from the following groups (I) and (II), respectively:
Group (I):
(1) 1-$R_1$-2-$R_2$-3-$R_3$-imidazolium ion ($R_1$ represents methyl group or butyl group, $R_2$ represents hydrogen or methyl group, $R_3$ represents an alkyl group and may contain a hetero atom),
(2) N—$R_4$-isoquinolium ion ($R_4$ represents an alkyl group and may contain a hetero atom),
(3) N—$R_5$-pridinium ion ($R_5$ represents an alkyl group and may contain a hetero atom),
(4) N,N—$R_6$,$R_7$-pyrrolidinium ion ($R_6$ represents methyl group, ethyl group, propyl group, isopropyl group, or butyl group, $R_7$ represents an alkyl group and may contain a hetero atom),
(5) N,N—$R_8$,$R_9$-piperidinium ion ($R_8$ represents methyl group or butyl group, $R_9$ is an alkyl group and may contain a hetero atom), or
(6) $R_{10}$,$R_{11}$,$R_{12}$,$R_{13}$-ammonium ion ($R_{10}$, $R_{11}$, $R_{12}$, and $R_{13}$ represents an alkyl group, a phenyl group, or a benzyl group independently, which may contain a hetero atom),
Group (II):
(1) Bis(trifluoromethanesulfonyl)imide ion,
(2) Triflate ion, or
(3) Bis(pentafluoroethanesulfonyl)imide ion.

14. The sensor chip according to claim 10, wherein,
the hydrophobic ionic liquid is selected from the followings:
1,3-Dimethylimidazolium bis(trifluoromethanesulfonyl)imide,
1-Ethyl-3-methylimidazolium bis(trifluoromethanesulfonyl)imide,
1-Ethyl-3-methylimidazolium triflate,
1-Ethyl-3-methylimidazolium bis(pentafluoroethane-sulfonyl)imide,
1,3-Diethylimidazolium bis(trifluoromethanesulfonyl)imide,
1,3-Diethylimidazolium triflate,
1-Butyl-3-ethylimidazolium triflate,
1,2-Dimethyl-3-ethylimidazolium bis(trifluoromethane-sulfonyl)imide,
1-Butyl-3-methylimidazolium bis(trifluoromethanesulfonyl)imide,
1-Butyl-3-methylimidazolium triflate,
1-isoPropyl-3-methylimidazolium bis(trifluoromethane-sulfonyl)imide,
1,2-Dimethyl-3-propylimidazolium bis(trifluoromethane-sulfonyl)imide,
N,N-Propylmethylpyrrolidinium bis(trifluoromethane-sulfonyl)imide,
Propyltrimethyammonium bis(trifluoromethanesulfonyl)imide,
N,N-Methylpropylpiperidinium bis(trifluoromethane-sulfonyl)imide, or
N-Butylpyridinium bis(trifluoromethanesulfonyl)imide.

15. The sensor chip according to claim 10, wherein, the cation and the anion comprised in the hydrophilic ionic liquid are selected from the following groups (I) and (III), respectively:

Group (I):

(1) 1-$R_1$-2-$R_2$-3-$R_3$-imidazolium ion ($R_1$ represents methyl group or butyl group, $R_2$ represents hydrogen or methyl group, $R_3$ represents an alkyl group and may contain a hetero atom), (2) N—$R_4$-isoquinolium ion ($R_4$ represents an alkyl group and may contain a hetero atom), (3) N—$R_5$-pridinium ion ($R_5$ represents an alkyl group and may contain a hetero atom), (4) N,N—$R_6$,$R_7$-pyrrolidinium ion ($R_6$ represents methyl group, ethyl group, propyl group, isopropyl group, or butyl group, $R_7$ represents an alkyl group and may contain a hetero atom), (5) N,N—$R_8$,$R_9$-piperidinium ion ($R_8$ represents methyl group or butyl group, $R_9$ is an alkyl group and may contain a hetero atom), or (6) $R_{10}$,$R_{11}$,$R_{12}$,$R_{13}$-ammonium ion ($R_{10}$, $R_{11}$, $R_{12}$, and $R_{13}$ represents an alkyl group, a phenyl group, or a benzyl group independently, which may contain a hetero atom), Group (III):

(4) Tetrafluoroborate ion, or (5) Halide ion.

16. The sensor chip according to claim 10, wherein, the hydrophilic ionic liquid is selected from the following:

1-Ethyl-3-methylimidazolium tetrafluoroborate,

1-Butyl-3-methylimidazolium tetrafluoroborate,

1-Methyl-3-propylimidazolium tetrafluoroborate,

1-Butyl-3-methylimidazolium iodide,

1-Hexyl-3-methylimidazolium bromide,

1-Hexyl-3-methylimidazolium chloride,

1-Octyl-3-methylimidazolium chloride, or

N-Hexylpyridinium chloride.

17. The sensor chip according to claim 10, wherein, the protection gel covers the entire of the stripping gel in such a manner that the stripping gel is hidden by the protection gel completely.

* * * * *